United States Patent [19]

Nohda

[11] 4,431,278
[45] Feb. 14, 1984

[54] EYE EXAMINING APPARATUS
[75] Inventor: Masao Nohda, Yokohama, Japan
[73] Assignee: Nippon Kogaku K.K., Tokyo, Japan
[21] Appl. No.: 240,139
[22] Filed: Mar. 3, 1981
[30] Foreign Application Priority Data
  Mar. 7, 1980 [JP] Japan .................................. 55-28030
[51] Int. Cl.³ ............................................. A61B 3/10
[52] U.S. Cl. ................................................ 351/211
[58] Field of Search ................. 351/6, 13, 14, 16, 205,
                                             351/211, 214, 221

[56] References Cited
U.S. PATENT DOCUMENTS
3,819,256  6/1974  Bellows et al. ....................... 351/6
4,190,332  2/1980  Body et al. .......................... 351/13

*Primary Examiner*—John K. Corbin
*Assistant Examiner*—Rodney B. Bovernick
*Attorney, Agent, or Firm*—Shapiro and Shapiro

[57] ABSTRACT

Improvements in an eye examining apparatus of the type having eye fixation mark means, eye refractive power measuring means and control means for moving an image of the fixation mark depending upon the output signal from said measuring means are disclosed. Said control means comprises means for detecting the position of the fixation mark image and means for detecting the difference between the level of signal from said position detecting means and the level of output from said measuring means. When the detected difference is within a predetermined range of values, the image of fixation mark is moved by a predetermined distance.

6 Claims, 7 Drawing Figures

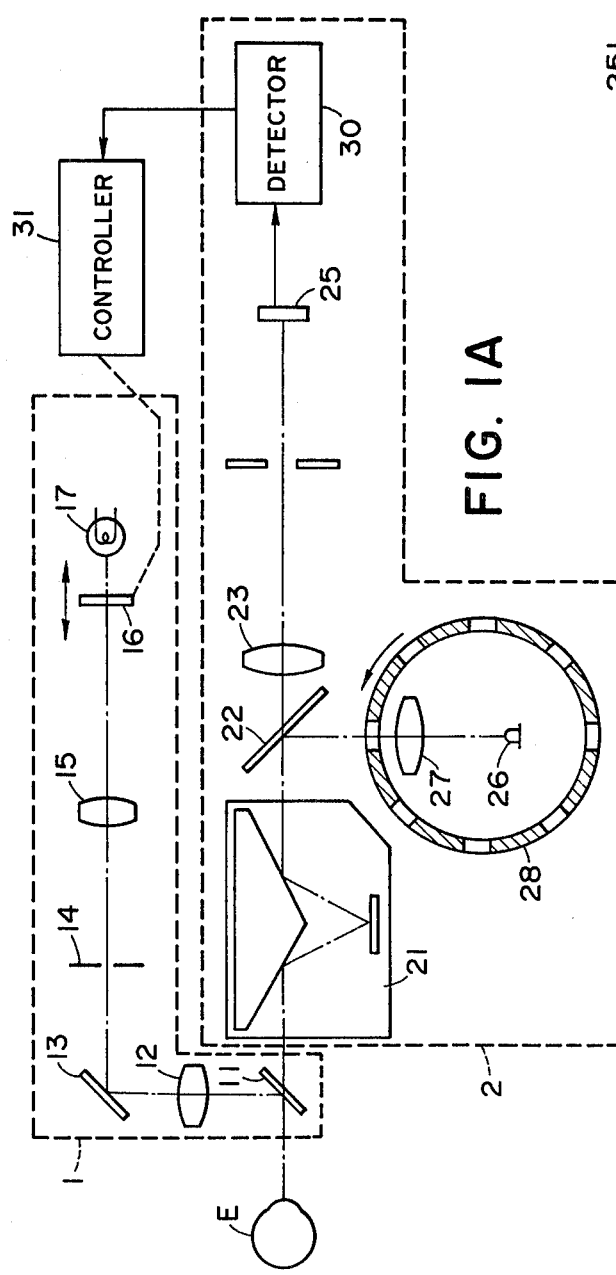
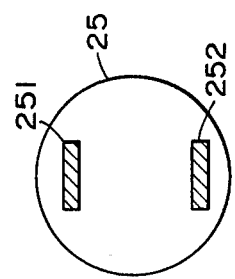
FIG. 1A
FIG. 1B

EYE EXAMINING APPARATUS

BACKGROUND OF THE INVENTION

1. Field of the Invention

The present invention generally relates to eye examining apparatus and more paticularly to apparatus for measuring eye refractive power which is provided with an optical system for forming an image of an eye fixation mark to effectively relax the sight regulation power of an eye to be examined.

2. Description of the Prior Art

An eye refractometer is an apparatus for measuring the refractive power or astigmatism of a eye in a state in which the sight regulation power acting on the examined eye is loosened. However, in practice, it is very difficult to relax the sight regulation power in eyes being examined. In general, the sight regulation power of human eyes has a tendency to spontaenously act when the eye looks into such eye examining apparatus. To solve the problem, the conventional eye refractometer has employed means for moving the image of the eye fixation mark in a direction such that the sight regulation power is loosened in an instant after setting the image at a certain finite distance. This conventional method of relaxing the sight regulation power involves some drawbacks. At the moment of the fixation mark image being moved, the person to be tested can hardly judge whether the image has been moved toward or away from him. As a result, he fails to perceive the image. Since the eye refractive power is measured in such state of the eye, it is apparent that a large error of measurement may be caused unless his eye is perfectly free of the sight regulation power at this moment.

SUMMARY OF THE INVENTION

Accordingly it is an object of the invention to provide an eye examining apparatus with which the sight regulation power of an eye to be examined can be changed effectively and suitably for examination.

It is a more specific object of the invention to provide an eye examining apparatus which comprises improved eye fixation mark means and improved eye refractive power measuring means to attain the effective change of sight regulation power of the examined eye.

To attain the above objects according to the invention there is provided in the measuring apparatus a driving means for moving the position of the fixation mark image continuously or stepwise depending upon the measured value of the eye refractive power. The value in diopter corresponding to the image position is compared with the value in diopter of the examined eye looking at the image. When the difference between the two values in diopter is within a predetermined range of values, the image position is further changed.

Other and further objects, features and advantages of the invention will appear more fully from the following description with reference to the accompanying drawings.

BRIEF DESCRIPTION OF THE DRAWINGS

FIG. 1A is a schematic side view of an embodiment of the eye examining apparatus according to the invention;

FIG. 1B is a plan view of the photo-electric member 25 used in the embodiment;

DESCRIPTION OF PREFERRED EMBODIMENT

Figure 2:
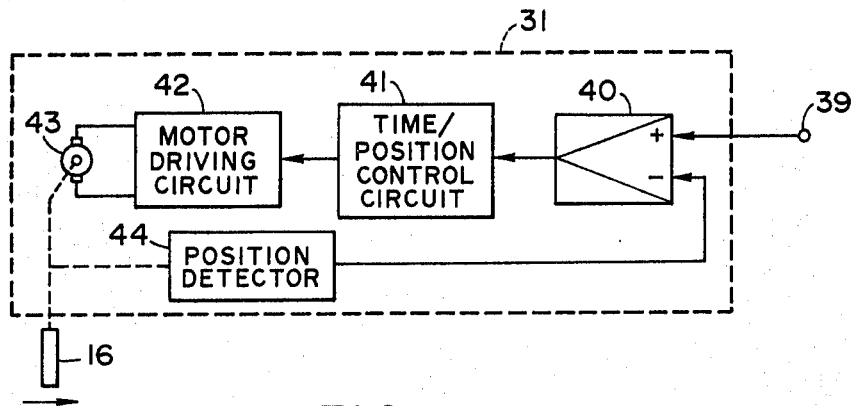
FIG. 2 is a block diagram showing a circuit form of the controller 31 used in the embodiment.

Referring first to FIGS. 1A and 1B a preferred embodiment of the invention is described in detail. FIG. 1A shows the basic arrangement of the eye examining apparatus comprising a sight regulation power relaxing unit 1 and an eye refractive power measuring unit 2. The unit 1 includes an optical system for forming an image of an eye fixation mark as later described in detail. The units 1 and 2 are united together to form a complete eye examining apparatus according to the invention.

Of the two units 1 and 2, the eye refractive power measuring unit 2 has been described fully in our prior application, Japanese Patent Application No. 69083/1979 and therefore only a brief explanation thereof will be given hereinafter.

In FIG. 1A, reference numeral 28 designates a rotary drum having slit openings. The drum 28 rotates, for example, in the direction of arrow in the drawing. A spot light source 26 is provided in the rotary drum 28. The beam of light from the spot light source is directed to an eye to be examined which is designated by E, through a projection lens 27, beam splitter 22 and image rotation prism 21. As the drum 28 rotates, the rays of light from the light source 26 are transformed into a linear beam of light which then falls upon the beam splitter 22. The beam of light enters the eye E through the beam splitter 22 and image rotation prism 21 and scans the fundus of the eye.

The image rotation prism 21 rotates about the optical axis and is so formed as to enable to obtain also scanning light suitable for measurement of astigmatism.

The reflected light from the fundus of the examined eye E enters again the image rotation prism and is transmitted to a photo-electric member 25 through the prism 21, beam splitter 22 and objective lens 23. As shown in FIG. 1B, the photo-electric member 25 has a pair of photo receptor elements 251 and 252 disposed spaced from the center of the member for producing various signals according to the behaviour of the reflected light from the fundus. These output signals are introduced into a detector 30 which carries out analog operations of the signals and then generates data of refractive power, astigmatism, etc. Data issued from the detector 30 are further processed by digital operation unit, memory, etc. (not shown). Since it is required for the present invention to know only the refractive power of the examined eye, we need not particularly consider the image rotation prism 21.

Hereinafter, the sight regulation power relaxing unit 1 will be described in detail.

The scanning light mentioned above reaches the fundus also through a beam splitter 11. At the same time, the eye E is looking at an eye fixation mark 16 through the beam splitter 11. In other words, the eye to be examined is observing, at this time, an image of the fixation mark 16 through relay lens 12 and objective lens 15.

Designated by 14 is a stop which is disposed conjugated with the cornea of the examined eye E. Reference numeral 17 is a light source for illuminating the eye fixation mark 16. The fixation mark 16 is mounted movably along the optical axis. All the factors of its movement such as the amount and speed of movement are controlled by a controller 31. The controller receives signals which are usually electric signals. The movement of the fixation mark 16 can be changed by suitably changing the state of the input signals to the controller 31. The direction in which the fixation mark 16 is to be moved is that for making the eye E relaxed. In the shown embodiment, the controller 31 receives output data from the detector 30 so that a correlation is produced between the movement of fixation mark 16 and the output data from the detector 30.

The detector 30 sucessively detects the refractive power of the examined eye E (which is referred to simply as dpt.=diopter). Data of the detected diopter are represented in terms of an electric value such as voltage. When the voltage is zero, this represents 0 dpt. The polarity of the voltage will express the sign (+, −) of the diopter and the absolute value of the voltage will express the value of diopter.

The eye E to be examined is observing an image of the fixation mark 16. Initially, the fixation mark 16 is preset at a position in which the distance between the fixation mark image and the eye E is finite and relatively short. When the eye E is fixed upon the fixation mark image, the detector 30 produces a diopter value detected at the time. The controller 31 receives the diopter value as an input from the detector 30 to drive, for example, a steppoing motor. The stepping-motor controlled by the controller 31 moves the fixation mark 16 up to a second position in which the distance between the mark image and the eye E becomes longer than that in the initial position. After the fixation mark 16 is set at the second position, the eye E begins looking at the fixation mark image. The diopter value detected by the detector 30 at the time of the eye E being completely fixed upon the fixation mark image is smaller than the diopter value previously detected in the initial set position. This means that the sight regulation power acting upon the eye E is being relaxed. In this manner, the fixation mark 16 is moved step by step to gradually relax the sight regulation power. By repeating this step, the eye E can be released from the sight regulation power effectively and surely.

The basic structure and the manner of operation of the controller 31 which enables the above movement of the fixation mark 16 are described hereinafter with reference to FIG. 2.

In FIG. 2, reference numeral 39 designates a terminal to which the output data is applied from the above described detector 30. Reference numeral 40 is a differential amplifier which receives as input the output data signal from the detector through the terminal 39 and the output signal from a position detector 44 and which amplifies the difference between the two input signals. The position detector 44 produces a signal as formed by adding or subtracting the amount of rotation of the fixation mark driving means such as stepping motor 43. The fixation mark 16 is moved by the motor 43 for a time and up to a position determined by a time/position control circuit 41. The time/position control circuit 41 receives as input the output signal from the differential amplifier 40 and comprises a comparator, integrator, monostable multivibrator etc. to move the fixation mark in a predetermined pattern. The output signal from the time/position control circuit 41 is applied to a motor driving circuit 42 to drive the motor 43.

For the purpose of explanation it is assumed that the fixation mark 16 is initially set to a preselected position and that diopter as measured when the eye E looked at the fixation mark 16 is −1.5 dpt. In this case, the position detector 44 produces a voltage proportional to −1.5 dpt. When the eye E is fixed upon the fixation mark 16 in this position of the detector, a voltage proportional to −1.5 dpt. is also applied to the terminal 39 and the output voltage from the amplifier 40 becomes about 0V. The time/position controller 41 detects this 0V and issues a signal or pulses for a certain definite time to drive the motor 43 into rotation. Thus, the fixation mark 16 is moved to a second set position such as the position of −1.0 dpt. For a certain time length from the second setting time point, the time/position control circuit 41 issues no signal irrespective of input thereto. During this period of time, the eye E tends to look at the fixation mark 16 set at −1.0 dpt. and the position detector 44 continues producing a voltage proportional to −1.0 dpt. Therefore, when the eye E reaches −1.0 dpt. the same operation as above is repeated so as to further move the fixation mark 16 to a third setting position. This operation is repeated until the fixation mark 16 is moved up to a position corresponding to 0 dpt. or +1.5 dpt. at which the sight regulation power becomes completely relaxed.

In the manner described above, the sight regulation power acting on the eye E to be examined is gradually relaxed with the movement of the fixation mark 16. However, at a point, the eye gets in a state in which the relaxation of the eye regulation power no longer follows the displacement of the fixation mark 16. When this state takes place, the fixation mark is stopped at the position. Therefore, diopter inherent in the tested person can be represented by the difference between the diopter corresponding to the stop position of the fixation mark and the diopter of the examined eye E detected at this time point. However, in this case there is a problem to be considered.

As previously mentioned, the time/position control circuit 41 is so formed as to detect 0V of the output voltage from the amplifier 40. The eye E fixed to the fixation mark will fluctuate tremulously and therefore the output data also will fluctuate in this case. Although such fluctuation of output data may be removed by using a filter circuit or the like to some extent, the state of detection is still apt to become unstable.

To solve the problem there is used in the time/position control circuit 41 a comparator with hysteresis or a window type comparator. The fixation mark is moved further by one step when both of the above two diopter values fall within a predetermined range of values. By doing so, it is possible to obtain the difference between the diopter value to be relaxed by the fixation mark 16 and the diopter value of the relaxed eye by means of the output voltage from the amplifier 40.

To complete the desired relaxation of sight regulation power more correctly and in a shorter time, the fixation mark 16 may be forcedly moved up to a position corresponding to 0 dpt. or +1.5 dpt. When the above two diopter values do not get within the predetermined range, that is, when the above mentioned followability of the eye relaxing motion to the displacement of the fixation mark is lost.

Figure 3A:
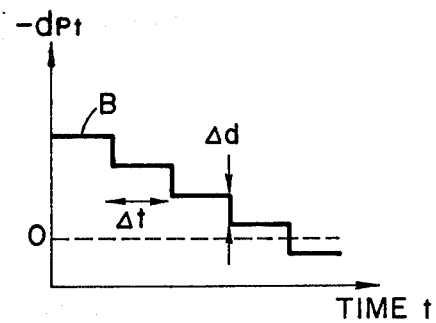
FIGS. 3A, 3B and 4A, 4B are graphs showing changes of eye fixation mark and relaxation of the examined eye with time.
Figure 3B:
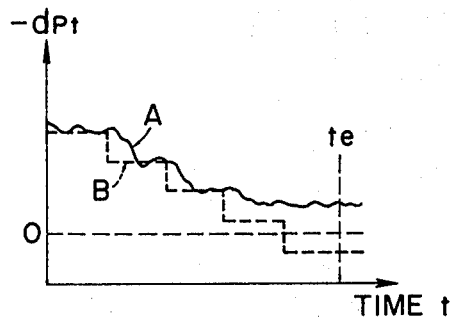

FIGS. 3A and 3B illustrate the manner in which the relaxation of sight regulation power can be attained in accordance with the above described embodiment.

FIG. 3A shows the change in position of the fixation mark 16 with time wherein positions of the fixation mark are plotted with the position in minus diopter as the ordinate and the time as the abscissa. FIG. 3B shows, as an example, the change in refractive power of the examined eye with the change in position of the fixation mark 16 plotted in the same manner as in FIG. 3A.

From FIG. 3B it is seen that at a time point of te the examined eye becomes almost completely relaxed and its refractive power changes no more. As shown in FIG. 3A, the position of fixation mark 16 is stepwisely changed by Δd. The width of hysteresis of the comparator in the time/position control circuit 41 described above is so selected as to correspond to the amount of change Δd in diopter of the fixation mark 16. At every step, as seen from FIG. 3B, the diopter value (B) of the fixation mark 16 and the diopter value (A) of the examined eye E are compared with each other. When the difference between the two values (A) and (B) is smaller than the amount of change Δd for one step, the fixation mark is further moved to the next step.

Of course, some physiological response time is required for the diopter (A) of the examined eye to follow the diopter (B) of the fixation mark 16 which is stepwisely changed. Further, the range of diopters within which the examined eye is able to follow the diopter of the fixation mark, the minimum diopter resolving power, possible minute fluctuation of the fixed eye, etc. must be taken into consideration in determining the amount of diopter change Δd and the rest time Δt of the fixation mark 16. Considering these factors it has been found that the following ranges of values are practically desirable for Δd and Δt:

$$0.5 \text{ dpt.} \leq \Delta d \leq 1.5 \text{ dpt.}$$

$$0.5 \text{ sec.} \leq \Delta t \leq 1.5 \text{ sec.}$$

The diopter inherent in the examined eye can be obtained by measuring the diopter (A) using the eye refractive power measuring unit 2 immediately after the fixation mark has stopped its moving at te.

According to the above embodiment wherein the fixation mark 16 is stepwise moved, it is possible to know the diopter of the examined eye for every step. However, such stepwise procedure is somewhat time consuming. In particular when the amount of change in position Δd is relatively large, a relatively long time is required for the examined eye to follow it. Accordingly, it is required to set a long time for the rest time Δt.

According to another embodiment of the invention, this drawback can be eliminated by moving the fixation mark 16 continously and stopping the movement of the fixation mark when the sight regulation power acting on the examined eye has been relaxed. This modification can be realized by using a DC motor or the like as the motor 43 shown in FIG. 2 and using, as the time/position control circuit 41, a circuit which produces always constant voltage so long as the output voltage from the amplifier 40 remains within a predetermined range of values.

Figure 4A:
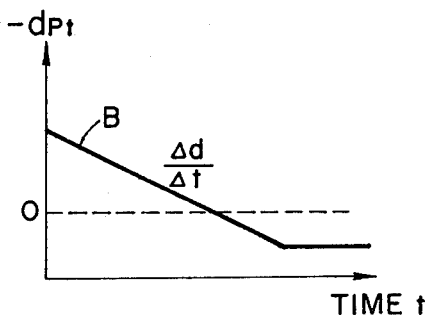
Figure 4B:
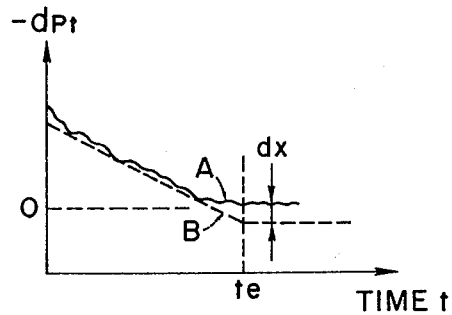

FIGS. 4A and 4B illustrate the manner in which the sight regulation power can be relaxed using such controller 31. Coordinates in FIGS. 4A and 4B correspond to those in FIGS. 3A and 3B. From FIG. 4B it is seen that the examined eye becomes almost completely relaxed at a time point of te and its refractive power remains unchanged after the time point te.

The diopter (B) of fixation mark 16 in this embodiment changes continously and linearly as shown in FIG. 4A. This diopter value (B) is proportional to the output signal from the position detector 44. Therefore, during the time when the tested person has fixed his eye E upon the fixation mark 16, the motor 43 continues rotating and the fixation mark 16 is moved at a constant speed. At a time point, the eye E becomes unable to look at the fixation mark, namely unable to follow the moving fixation mark 16. This means that the relaxation of eye has just been completed at that time point.

Since, as previously noted, the comparator in the time/position control circuit 41 has hysteresis, the fixation mark 16 stops while keeping a predetermined difference between the diopter of the fixation mark and that of the relaxed eye as shown in FIG. 4B. In FIG. 4B, dx is the difference between the diopter (B) of the fixation mark 16 and the diopter (A) of the examined eye existing at the time when the fixation mark 16 stops moving. This difference dx corresponds to the width of above mentioned hysteresis and also corresponds to the output voltage from the amplifier 40. Therefore, in this case, the diopter value inherent in the examined person can be found out by making known only the output signal from the position detector 44. Since the width of hysteresis can be selected optionally it is allowed to suitably select the difference dx taking into account other factors such as the tremor of the fixed eye. Also, in this embodiment, the eye refractive power measuring unit 2 measures the diopter of the examined eye immediately after the time point te at which the fixation mark 16 stops moving.

As for the rate of change Δd/Δt of the diopter (B) shown in FIG. 4A, that is, the moving speed of the fixation mark 16, it should be understood that the moving speed need not be determined as a single and fixed value. For example, it may be variable according to age and sex of the person to be tested so as to accommodate the moving speed of the fixation mark to the physiological and psychological actions inherent in the tested person.

While the invention has been particularly shown and described with reference to preferred embodiments thereof, it is to be understood that the invention is never limited to such embodiments only. Obviously many modifications and variations of the present invention are possible in the light of the above teachings. For example, in the first embodiment in which the fixation mark is stepwisely moved, the number of steps may be increased by reducing Δd and Δt to such extent that the fixation mark apparently looks as if moved continuously. Also, in the second embodiment in which the fixation mark is continuously moved, the fixation mark may be moved logarithmically instead of being moved linearly.

While in the above embodiments the relaxation of an eye to be examined has been particularly described, the measuring apparatus of the present invention can be used also to measure the refractive power of a tensioned eye. In this case, the eye to be examined is strained by moving the fixation mark in the direction opposite to that for relaxing the eye described above, namely in the direction of the negative diopter being increased. In this manner it is possible to measure the refractive power of the examined eye also at the shortest distance. In this case also the fixation mark is further moved when the difference between the diopter of the fixation mark and the diopter of the examined eye is within a predetermined range of values.

As readily understood from the above embodiments, instead of moving the fixation mark, a part of the optical system for forming an image of the fixation mark may be moved. For example, the lens 15 in the above embodiments may be moved while keeping the fixation mark at a fixed position.

As seen from the foregoing, the measuring apparatus according to the invention enables to surely and effectively change the sight regulation power acting on an eye to be examined. Therefore, correct measurement of common eye refractive power can be carried out for completely relaxed eyes without failure. Furthermore, according to the invention, the relaxation of an eye to be examined necessary before measurement is carried out considering physiological phenomenons of eyes. Therefore, the psychological stress on the tested person during relaxation can be minimized.

What I claim is:

1. An eye examining apparatus comprising fixation mark means for forming an image of an eye fixation mark which an eye to be examined looks at, means for measuring the refractive power of said examined eye, and control means for moving said fixation mark image in a direction so as to relax or strain the sight regulation power acting on said examined eye in accordance with an output signal from said measuring means, characterized in that said control means comprises position detector means for detecting the position of said fixation mark image and for providing a position signal representative of the position and difference detector means for detecting a difference in level between the position signal from said position detector means and the output signal from said measuring means and for causing the control means to move said fixation mark image a predetermined amount when said difference falls within a predetermined range of values.

2. An eye examining apparatus as set forth in claim 1, which is characterized in that said control means comprises further a time/position controller for moving the position of said fixation mark image repeatedly by the predetermined amount in response to said difference detector means and for holding said fixation mark image in each position for a predetermined time after said predetermined amount of movement of said fixation mark image, thereby moving said fixation mark image stepwisely starting from a predetermined position.

3. An eye examining apparatus as set forth in claim 2, which is characterized in that said predetermined amount by which said fixation mark image is moved by said time/position controller is in a range of distances which said examined eye can substantially follow and that said holding time is a time required for said examined eye to substantially look at said fixation mark image.

4. An eye examining apparatus as set forth in claim 3, which is characterized in that said fixation mark image is moved in the direction of said examined eye being relaxed and that said amount of movement $\Delta d$ and said holding time $\Delta t$ are so selected as to satisfy the following conditions:

$$0.5 \text{ dpt.} \leq \Delta d \leq 1.5 \text{ dpt.}$$

$$0.5 \text{ sec.} \leq \Delta t \leq 1.5 \text{ sec.}$$

where dpt. represents diopter.

5. An eye examining apparatus as set forth in claim 1, wherein said control means includes means for moving the fixation mark image continuously in said direction.

6. An eye examining apparatus as set forth in claim 1, wherein said fixation mark image is moved in a direction so as to relax said examined eye, and wherein said control means includes means responsive to the examined eye becoming relaxed so as to stop the movement of the fixation mark image.

* * * * *